US006556854B1

(12) United States Patent
Sato et al.

(10) Patent No.: US 6,556,854 B1
(45) Date of Patent: Apr. 29, 2003

(54) BLOOD VESSEL IMAGING SYSTEM USING HOMODYNE AND HETERODYNE EFFECTS

(75) Inventors: Tomoo Sato, Kaisei-machi (JP);
Masahiro Toida, Kaisei-machi (JP);
Kazuhiro Tsujita, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/495,758

(22) Filed: Feb. 1, 2000

Related U.S. Application Data

(63) Continuation-in-part of application No. 09/444,381, filed on Nov. 22, 1999, now abandoned.

(30) Foreign Application Priority Data

| Nov. 20, 1998 | (JP) | 10-331292 |
| Nov. 20, 1998 | (JP) | 10-331409 |
| Nov. 22, 1999 | (JP) | 11-331497 |

(51) Int. Cl.[7] ............................................... A61B 5/05
(52) U.S. Cl. ................ 600/407; 600/428; 600/310; 600/476; 600/500; 600/502; 600/504; 356/319; 356/450; 356/484; 356/27; 356/28; 356/28.5
(58) Field of Search .................. 600/300, 407, 600/419, 437, 476–80, 473; 356/27–29, 484, 28.5; 128/916, 898

(56) References Cited

U.S. PATENT DOCUMENTS

| 3,915,572 A | * 10/1975 | Orloff | 356/28 |
| 4,026,655 A | 5/1977 | Gunter, Jr. | 356/28 |
| 4,109,647 A | * 8/1978 | Stern et al. | 356/28 |
| 4,168,906 A | * 9/1979 | Schwiesow | 356/28 |
| 4,590,948 A | * 5/1986 | Nilsson | 600/479 |
| 4,834,111 A | 5/1989 | Khanna et al. | 600/587 |
| 5,709,210 A | * 1/1998 | Green et al. | 600/453 |
| 5,778,878 A | * 7/1998 | Kellam | 600/310 |
| 5,946,092 A | 8/1999 | DeFreez et al. | 356/336 |
| 6,043,655 A | * 3/2000 | Makita et al. | 324/307 |
| 6,305,804 B1 | * 10/2001 | Rice et al. | 351/221 |
| 6,374,128 B1 | 4/2002 | Toida et al. | 600/310 |

OTHER PUBLICATIONS

B. Devaraj et al., Recent Advances in Coherent Detection Imaging (CDI) in Biomedicine: Laser Tomography of Human Tissues in Vivo and In Vitro, IEEE Journal of Selected Topics in Quantum Electronics, vol. 2, pp. 1008, 1996.

Kohichi Shimizu et al., "Possibility of Optical Fluoroscopy of Biological Organisms and Functional Imaging," *Japanese ME Academy Magazine BME*, vol. 8, No. 55, (1994), pp. 41–50.

* cited by examiner

*Primary Examiner*—Marvin M. Lateef
*Assistant Examiner*—Barry Pass
(74) *Attorney, Agent, or Firm*—Sughrue Mion, PLLC

(57) ABSTRACT

A homodyne interference system splits first and second light beams from a common light source and causes the first and second light beams to impinge upon an irradiating point of an organism at different directions. An optical heterodyne system splits a third beam from the common light source and imparts a frequency shift to the third beam. The outputs of the homodyne and heterodyne systems combine to permit extraction of a beat component of the homodyne system at a high SNR level. The output of the homodyne and heterodyne system are output as an image, which may be timed to a phase timing mechanism to provide an improved output.

10 Claims, 11 Drawing Sheets

$\vec{V}$ : FLOW RATE VECTOR TO BE MEASURED $\vec{V_1}, \vec{V_2}$ : FLOW RATE VECTORS MEASURED

BLOOD VESSEL IMAGING SYSTEM USING HOMODYNE AND HETERODYNE EFFECTS

This application is a continuation-in-part application of application Ser. No. 09/444,381 filed Nov. 22, 1999 now abandoned.

BACKGROUND OF THE INVENTION

1. Field of the Invention

This invention relates to a blood vessel imaging system for imaging blood vessels, and more particularly to a blood vessel imaging system which can image blood vessels with arteries and veins distinguished from each other. This invention also relates to a system for distinguishing arteries and veins from each other. This invention further relates to a system for measuring a frequency deviation of a measuring light beam, which has been irradiated to a scattering fluid for blood vessel imaging, or the like, due to a Doppler effect.

2. Description of the Related Art

In the clinical field, there has been a wide demand for imaging arteries and veins clearly distinguished from each other. For example, since arteriosclerosis generally starts at the periphery of the arteries, it will be useful in diagnosing arteriosclerosis if the inner walls of the peripheral arteries can be imaged distinguished from those of the veins.

There has been wide known angiography as a system for imaging blood vessels. However angiography is invasive, e.g., it involves administration of a contrast medium to the testee, which gives the testee causalgia and involves insertion of a catheter into an artery, and accordingly, it is difficult to perform angiography without staying the testee in the hospital.

Further there has been proposed technique for imaging a part of an organism on the basis of penetration of light through the part as disclosed in "IEEE Journal of Selected Topics in Quantum Electronics", Vol. 2, p1008, 1996. In this imaging method, a light beam is projected onto a finger and light which travels straight through the finger while scattered in multiple scattering in the finger is detected by optical heterodyne detection. Then a cross-sectional image of the finger is obtained by use of a method of image reconstitution which has been employed in computed tomography. However, it has been impossible to recognize existence of a blood vessel by this method.

Further, there has been proposed technique in which the hollow of a hand is illuminated by light emitted from a plurality of LEDs and an image of blood vessels on the back side of the hand formed by light scattered inside the hand is taken as animation by a sensitive TV camera as disclosed in "Japanese ME Academy Magazine BME", vol.8, No.5, pp.41, 1994. However, only subcutaneous veins or blood vessels in a relatively shallow part of the hand can be imaged by the technique and it is impossible to image arteries and veins clearly distinguished from each other by the technique.

SUMMARY OF THE INVENTION

In view of the foregoing observations and description, the primary object of the present invention is to provide a blood vessel imaging system which can image peripheral blood vessels such as peripheral arteries and the like in a relatively deep part of the hand or foot with the blood vessels clearly distinguished from other soft tissues and can image blood vessels with arteries and veins clearly distinguished from each other without exposing the testee to heavy load.

Another object of the present invention is to provide a system which can clearly distinguish arteries and veins from each other without exposing a testee to heavy load.

The specific object of the present invention is to provide a system which can measure a frequency deviation of a measuring light beam, which has been irradiated to a scattering fluid, due to a Doppler effect.

In blood vessel imaging systems in accordance with one aspect of the present invention, a blood vessel is basically imaged by projecting a measuring light beam onto an organism and detecting light scattered by the organism. A light homodyne detection system is applied in detecting the scattered light, thereby distinguishing an artery and a vein from each other on the basis of difference in flow rate of the blood between the artery and the vein. Further by combining the light homodyne detection system with an optical heterodyne detection system, the beat components of light detected by the light homodyne detection system are amplified.

That is, in accordance with a first aspect of the present invention, there is provided a blood vessel imaging system comprising a measuring light source which emits a measuring light beam, an optical homodyne interference system which splits first and second light beams from the measuring light beam, causes the first and second light beams to impinge upon the same irradiating point on an organism in different directions, and combines together the first and second light beams scattered at the irradiating point into a combined scattered light beam, a scanning means which causes the first and second light beams to scan the organism, an optical heterodyne detection system consisting of an optical heterodyne interference system which splits a third light beam from the measuring light beam and combines the third light beam with the combined scattered light beam emanating from the optical homodyne interference system into a combined output light beam, a frequency shifter which causes a frequency difference between the third light beam and the first and second light beams, and a beat component detecting means which detects beat components of the combined output light beam and outputs a beat component detection signal, and an image signal generating means which generates an image signal on the basis of the frequency of the beat components, generated by the optical homodyne interference system, included in the beat component detection signal output from the optical heterodyne detection system.

For example, the image signal generating means generates an image signal representing artery parts of the organism when the frequency of the beat components generated by the optical homodyne interference system is higher than a predetermined threshold value, and generates an image signal representing vein parts of the organism when the frequency of the beat components generated by the optical homodyne interference system is not higher than the predetermined threshold value.

It is preferred that the blood vessel imaging system be provided with a position adjustment means which adjusts the positions of the organism and the optical homodyne interference system relative to each other to change the directions of incidence to the irradiating point of the first and second light beams.

It is preferred that the blood vessel imaging system be provided with an in-phase time detecting means for detecting in-phase times, at which the flow rate of blood in the blood vessel to be imaged becomes a predetermined value, and outputting a timing signal, and the image signal generating means samples the beat component detection signal at times, at which the flow rate of the blood is substantially maximized, on the basis of the timing signal and generates the image signal on the basis of the sampled beat component detection signal.

The in-phase time detecting means may be, for instance, a means for detecting the pulse wave of the organism, or a means for detecting the times at which the frequency of the beat components generated by the optical homodyne interference system takes a peak value.

When fluid is flowing in the irradiating point upon which the first and second light beams impinge in different directions, the frequencies of the first and second light beams scattered at the irradiating point are deviated by a Doppler effect.

Assuming, for the purpose of simplicity, that one of the first and second light beams passes through one of two points on a plane facing the organism and travels along an optical path passing through the optical axis after scattered and reflected by the organism and the other of the first and second light beams passes through the other of two points and travels along an optical path passing through the optical axis after scattered and reflected by the organism, frequency deviation of said one of the first and second light beams is $\Delta f$ and that of the other is $-\Delta f$ when the reflecting point has a velocity component. When the scattered first and second light beams are combined, a beat component at a frequency of $2\Delta f$ is generated by interference in the combined scattered light beam.

Accordingly, when existence of a beat component at a frequency of $2\Delta f$ is detected for each scanning point of the measuring light beam (the first and second light beams) and the image signal generating means is arranged to generate, an image signal component bearing thereon a relatively high density when the beat component is detected and an image signal component bearing thereon a relatively low density when the beat component is not detected, the part through which fluid is flowing, that is, the blood vessel part, can be imaged at a high density whereas other soft tissues are imaged at a low density.

The artery part and the vein part can be distinguished from each other in the following manner. That is, the frequency deviation $\Delta f$ is in proportion to the flow rate of the fluid and the flow rate of blood is higher in arteries than in veins. Accordingly, the frequency deviation $\Delta fa$ when the measuring light beam is projected onto an artery is larger than the frequency deviation $\Delta fv$ when the measuring light beam is projected onto a vein. Accordingly, when a suitable threshold value is set with respect to the frequency $2\Delta f$ of the beat component detection signal (beat signal), and the image signal generating means is arranged so that it generates an image signal representing an artery part when the beat signal frequency $2\Delta f$ is higher than the threshold value and generates an image signal representing a vein part when the beat signal frequency $2\Delta f$ is not higher than the threshold value, the artery part and the vein part can be imaged distinguished from each other.

When the image signal generating means is arranged to generate an image signal bearing thereon a density which is higher as the value of the beat signal frequency $2\Delta f$ becomes higher without use of a threshold value, the artery part and the vein part can be imaged so that they can be distinguished from each other by density (brightness).

Since the measuring light beam scattered by a blood vessel is inherently very weak, the beat signal is also very weak. However, in the blood vessel imaging system of the present invention, since the beat signal output from the optical heterodyne detecting system is detected, the amplitude of the signal representing the beat components generated by the optical homodyne interference system is superimposed with the beat components generated by the optical heterodyne detection system and is theoretically amplified to $(A2/A1)^{1/2}$ times wherein A1 represents the amplitude of the beat signal by the homodyne detection system and A2 represents the amplitude of the beat signal by the heterodyne detection system. Since the amount of light in the heterodyne detecting system can be freely set, the beat signal can be detected at a high S/N ratio by properly setting the amount of light, whereby even a peripheral artery or the like deep in the hand or foot can be clearly imaged.

Further, when a position adjustment means which adjusts the positions of the organism and the optical homodyne interference system relative to each other to change the directions of incidence to the irradiating point of the first and second light beams is provided, the beat signal can be detected at a higher S/N ratio.

That is, assuming that the first and second light beams impinge upon the organism passing through two points on a plane opposed to the organism, the amplitude of the beat signal generated by the optical homodyne interference system is maximized when the flow of blood is in a direction parallel to the straight line joining the two points. By setting the directions of incidence of the first and second light beams to be parallel to the flow of blood by operating the position adjustment means, a high level beat signal can be obtained.

When so setting the directions of incidence of the first and second light beams, it is not necessary to watch the directions of incidence and the direction of the flow of blood but the position adjustment means has only to be operated so that the intensity of the beat signal is maximized.

The flow rate of arterial blood varies with pulsation and sometimes becomes very close to that of the venous blood. Accordingly, when the beat components are detected at the minimum flow rate of arterial blood, an artery and a vein sometimes cannot be clearly distinguished from each other.

When the blood vessel imaging system is provided with an in-phase time detecting means for detecting in-phase times, at which the flow rate of blood in the blood vessel to be imaged becomes a predetermined value, and outputting a timing signal, and the image signal generating means samples the beat component detection signal at times, at which the flow rate of the blood is substantially maximized, on the basis of the timing signal and generates the image signal on the basis of the sampled beat component detection signal, the image signal can be constantly generated on the basis of a beat signal at a time at which the flow rate of the arterial blood is maximized, whereby the aforesaid problem can be avoided.

In blood vessel imaging systems in accordance with another aspect of the present invention, a blood vessel is basically imaged by projecting a measuring light beam onto an organism and detecting light scattered by the organism. An artery and a vein are distinguished from each other on the basis of difference in direction of flow of blood between the artery and the vein by use of an optical interference system. Further by combining the light homodyne detection system with the optical interference system, the beat components of light detected by the optical interference system are amplified.

That is, in accordance with a second aspect of the present invention, there is provided a blood vessel imaging system comprising a measuring light source which emits a measuring light beam, an optical interference system consisting of a first optical system which splits first and second light beams from the measuring light beam, causes the first and second light beams to impinge upon the same irradiating point on an organism in different directions, and combines together the first and second light beams scattered at the irradiating point into a combined scattered light beam, and a first frequency shifter which causes a frequency difference between the first and second light beams, a scanning means which causes the first and second light beams to scan the organism, an optical heterodyne detection system consisting of a second optical system which splits a third light beam from the measuring light beam upstream of the first optical system and combines the third light beam with the combined scattered light beam emanating from the first optical system into a combined output light beam, a second frequency shifter which causes a frequency difference between the third light beam and the measuring light beam from which the third light beam is split, and a beat component detecting means which detects beat components of the combined output light beam and outputs a beat component detection signal, and an image signal generating means which generates an image signal on the basis of the frequency of the beat components, generated by the optical interference system, included in the beat component detection signal output from the optical heterodyne detection system.

For example, the image signal generating means generates an image signal representing artery parts of the organism when the frequency of the beat components generated by the optical interference system is higher than a predetermined threshold value, and generates an image signal representing vein parts of the organism when the frequency of the beat components generated by the optical interference system is not higher than the predetermined threshold value.

It is preferred that the blood vessel imaging system be provided with a position adjustment means which adjusts the positions of the organism and the optical interference system relative to each other to change the directions of incidence to the irradiating point of the first and second light beams.

Instead of providing such a position adjustment means, an additional optical interference system having the same arrangement as said (first) optical interference system may be provided so that the directions in which the first and second light beams of one of the optical interference systems impinge upon the irradiating point are directions which extend along an x-direction on a plane opposed to the irradiating point when projected onto the plane, and the directions in which the first and second light beams of the other of the optical interference systems impinge upon the irradiating point are directions which extend along a y-direction perpendicular to the x-direction on said plane when projected onto the plane, and in this case, the image signal generating means generates an image signal on the basis of the value of $fx^2+fy^2$ wherein fx and fy represent the frequency deviations of the beat components generated by the respective optical interference systems.

Also, instead of providing such a position adjustment means, an additional optical interference system having the same arrangement as said (first) optical interference system may be provided so that the directions in which the first and second light beams of one of the optical interference systems impinge upon the irradiating point are directions which extend along a straight line on a plane opposed to the irradiating point when projected onto the plane, and the directions in which the first and second light beams of the other of the optical interference systems impinge upon the irradiating point are directions which extend along a direction making an angle of θ, where 0°<θ<90°, with said straight line on said plane when projected onto the plane, and in this case, the image signal generating means generates an image signal on the basis of the values of fx' and fy' wherein fx' and fy' represent the frequency deviations of the beat components generated by the respective optical interference systems. It is preferred that also the blood vessel imaging system in accordance with the second aspect of the present invention be provided with an in-phase time detecting means for detecting in-phase times, at which the flow rate of blood in the blood vessel to be imaged becomes a predetermined value, and outputting a timing signal, and the image signal generating means samples the beat component detection signal at times, at which the flow rate of the blood is substantially maximized, on the basis of the timing signal and generates the image signal on the basis of the sampled beat component detection signal.

The in-phase time detecting means may be, for instance, a means for detecting the pulse wave of the organism, or a means for detecting the times at which the frequency of the beat components generated by the optical homodyne interference system takes a peak value. As described above, when fluid is flowing in the irradiating point upon which the first and second light beams impinge in different directions, the frequencies of the first and second light beams scattered at the irradiating point are deviated by a Doppler effect.

Assuming, for the purpose of simplicity, that one of the first and second light beams passes through one of two points on a plane facing the organism and travels along an optical path passing through the optical axis after scattered and reflected by the organism and the other of the first and second light beams passes through the other of the two points and travels along an optical path passing through the optical axis after scattered and reflected by the organism while the frequency of said one of the first and second light beams is $\omega+\Delta\omega$ and the frequency of said the other of the first and second light beams is ω (αω is the amount of the frequency shift by the first frequency shifter), frequency of said one of the first and second light beams is shifted to $\omega+\Delta\omega+fa$ (fa being the amount of frequency deviation) and that of the other is shifted to ω−fa. When the scattered first and second light beams are combined, a beat component at a frequency of $\{(\omega+\Delta\omega+fa)-(\omega-fa)\}=\Delta\omega+2fa$ is generated by interference in the combined scattered light beam. When the direction of flow of the fluid is reverse and the amount of frequency deviation at that time is represented by fv, a beat component at a frequency of $\{(\omega+\Delta\omega-fv)-(\omega+fv)\}=\Delta\omega-2fv$ is generated by interference in the combined scattered light beam.

Since in the finger and the like, arterial blood and venous blood flow substantially in opposite directions, the frequency of the beat components when the measuring light beam (the first and second light beams) is being projected onto an artery part differs from that when the measuring light beam (the first and second light beams) is being projected onto a vein part in the manner described above.

Accordingly, when a suitable threshold value, e.g., equivalent to ω, is set with respect to the frequency of the beat component detection signal (beat signal), and the image signal generating means is arranged so that it generates an image signal representing an artery part when the beat signal frequency is higher than the threshold value and generates an image signal representing a vein part when the beat signal frequency is not higher than the threshold value, the artery part and the vein part can be imaged distinguished from each other.

Depending on the relation of the directions of incidence of the first and second light beams and the directions of flow of arterial blood and venous blood, the frequency of the beat component detection signal is deviated to reduce the amount of frequency shift $\Delta\omega$ when the first and second light beams are projected onto an artery part and to increase the amount of frequency shift $\Delta\omega$ when the first and second light beams are projected onto a vein part conversely to the case described above.

When the image signal generating means is arranged to generate an image signal bearing thereon a density which is higher as the value of the beat signal frequency becomes higher without use of a threshold value, the artery part and the vein part can be imaged so that they can be distinguished from each other by density (brightness).

Since the measuring light beam scattered by a blood vessel is inherently very weak, the beat signal is also very weak. However, in the blood vessel imaging system of the present invention, since the beat signal output from the optical heterodyne detecting system is detected, the amplitude of the signal representing the beat components generated by the optical interference system is superimposed with the beat components generated by the optical heterodyne detection system and is theoretically amplified to $(A2/A1)^{1/2}$ times wherein A1 represents the amplitude of the beat signal by the optical interference system and A2 represents the amplitude of the beat signal by the heterodyne detection system. Accordingly, the beat signal can be detected at a high S/N ratio and even a peripheral artery or the like deep in the hand or foot can be clearly imaged.

Further, when a position adjustment means which adjusts the positions of the organism and the optical interference system relative to each other to change the directions of incidence to the irradiating point of the first and second light beams is provided, the beat signal can be detected at a higher S/N ratio.

That is, assuming that one of the first and second light beams passes through one of two points on a plane facing the organism and travels along an optical path passing through the optical axis after scattered and reflected by the organism and the other of the first and second light beams passes through the other of two points and travels along an optical path passing through the optical axis after scattered and reflected by the organism, the amplitude of the beat signal generated by the optical interference system is maximized when the flow of blood is in a direction parallel to the straight line joining the two points. By setting the directions of incidence of the first and second light beams to be parallel to the flow of blood by operating the position adjustment means, a high level beat signal can be obtained.

When so setting the directions of incidence of the first and second light beams, it is not necessary to watch the directions of incidence and the direction of the flow of blood but the position adjustment means has only to be operated so that the intensity of the beat signal is maximized.

When an additional optical interference system having the same arrangement as said (first) optical interference system is provided so that the directions in which the first and second light beams of one of the optical interference systems impinge upon the irradiating point are directions which extend along a x-direction on a plane opposed to the irradiating point when projected onto the plane, and the directions in which the first and second light beams of the other of the optical interference systems impinge upon the irradiating point are directions which extend along a y-direction perpendicular to the x-direction on said plane when projected onto the plane, and the image signal generating means generates an image signal on the basis of the value of $fx^2+fy^2$ wherein fx and fy represent the frequency deviations of the beat components generated by the respective optical interference systems, a high level beat signal can be obtained irrespective of the directions of incidence of the first and second light beams relative to the direction of flow of blood.

That is, when there is a flow of blood in an arbitrary direction with respect to the x- and y-directions and the flow rate (velocity) is v, $v^2=vx^2+vy^2$, wherein and vx represents the velocity component in x-direction and vy represents the velocity component in y-direction, as shown in FIG. 16. Since the frequency deviations fx and fy are respectively proportional to vx and vy, generation of the image signal on the basis of $fx^2+fy^2$ is equivalent to generation of the image signal on the basis of $v^2$, or v, and is after all equivalent to generation of the image signal on the basis of the beat signal frequency when Doppler effect is generated only in the direction of the flow rate v. The case where Doppler effect is generated only in the direction of the flow rate v occurs when the directions of incidence of the first and second light beams are set to be parallel to the flow of blood.

In cases where the x direction and the y direction are perpendicular to each other, the effects described above are obtained. Arteries and veins can be imaged by being distinguished from each other also with the blood vessel imaging system in accordance with the second aspect of the present invention, wherein an additional optical interference system having the same arrangement as said (first) optical interference system is provided so that the directions in which the first and second light beams of one of the optical interference systems impinge upon the irradiating point are directions which extend along a straight line (an x' direction) on a plane opposed to the irradiating point when projected onto the plane, and the directions in which the first and second light beams of the other of the optical interference systems impinge upon the irradiating point are directions which extend along a direction (a y' direction) making an angle of $\theta$, where $0°<\theta<90°$, with said straight line on said plane when projected onto the plane. How the effects can be obtained will be described hereinbelow.

The x' direction and the y' direction described above are defined as shown in FIG. 17. Also, the flow rate (velocity) component in the x' direction is represented by $v_1$, and the flow rate component in the y' direction is represented by $v_2$. The angle made between the x' direction and the y' direction is represented by $\theta$, where $0°<\theta<90°$, and the angle made between the x' direction and the flow direction of blood is represented by $\phi$. The flow rate of blood v and the flow direction of blood $\phi$ can be calculated in the manner described below. From FIG. 17, Formulas (1) and (2) shown below obtain.

$$v_1 = v\cos\phi - v\sin\phi \times \frac{\cos\theta}{\sin\theta} \qquad (1)$$

-continued $$v_2 = v\sin\phi \times \sqrt{1^2 + \tan^2(90° - \theta)} \quad (2)$$

$$= v\sin\phi \times \sqrt{1 + \frac{\cos^2\theta}{\sin^2\theta}}$$

$$= v\sin\phi \times \frac{1}{\sin\theta}$$

From Formula (2) shown above, Formula (3) shown below obtains.

$$v \sin \phi = v_2 \sin \theta \quad (3)$$

Substitution of Formula (3) into Formula (1) yields $$v_1 = v\cos\phi - (v_2\sin\theta) \times \frac{\cos\theta}{\sin\theta} \quad (4)$$

$$v\cos\phi = v_1 + v_2\cos\theta$$

Also, $v^2 = (v \cos \phi)^2 + (v \sin \phi)^2$. Substitution of Formula (4) into this formula yields $$v^2 = (v_1 + v_2\cos\theta)^2 + (v_2\sin\theta)^2$$

$$= v_1^2 + 2v_1v_2\cos\theta + v_2^2$$

Also, the formula shown below obtains.

$$\tan\phi = \frac{v\sin\theta}{v\cos\theta}$$

Substitution of Formulas (3) and (4) into this formula yields $$\tan\phi = \frac{v\sin\theta}{v\cos\theta} = \frac{v_2\sin\theta}{v_1 + v_2\cos\theta}$$

From the two formulas mentioned last, Formulas (a) and (b) shown below obtain.

$$v = v_1^2 + 2v_1v_2 \cos \theta$$
$$+ v_2^2 \quad (a)$$

$$\tan\phi = \frac{v_2\sin\theta}{v_1 + v_2\cos\theta} \quad (b)$$

The flow rate of blood v and the flow direction of blood φ can be calculated with Formulas (a) and (b). When the flow rate of blood v is known, as described above, the artery and the vein can be imaged by being distinguished from each other in accordance with the difference between the flow rate of blood through the artery and the flow rate of blood through the vein.

In accordance with a third aspect of the present invention, there is provided a blood vessel distinguishing system comprising a measuring light source which emits a measuring light beam impinging upon an organism, a first optical interference system constituted such that a frequency of first beat components, which are generated by the measuring light beam and which are detected, changes in accordance with a flow rate of blood due to a Doppler effect with the blood flow, a second optical interference system for causing signal light and a local oscillator beam, which has been modulated with a frequency different from the frequency of the first beat components detected by the first optical interference system, to interfere with each other, and thereby generating second beat components having a frequency different from the frequency of the first beat components, a deviation measuring means for measuring a frequency deviation of a beat signal, which is formed by the second beat components, from the modulation frequency of the local oscillator beam, and a distinguishing means for distinguishing whether a blood vessel containing the blood flow is an artery or a vein, the distinguishing being made in accordance with relationship between a magnitude of the frequency deviation, which has been measured by the deviation measuring means, and a predetermined threshold value.

It is preferred that the blood vessel distinguishing system be provided with a position adjustment means which adjusts the positions of the organism and the first optical interference system relative to each other to change the directions of incidence to the same irradiating point of first and second light beams, into which the measuring light beam is split.

Also, the blood vessel distinguishing system should preferably be modified such that an additional first optical interference system having the same arrangement as said first optical interference system may be provided so that the directions in which first and second light beams split from the measuring light beam in one of the first optical interference systems impinge upon the irradiating point are directions which extend along a straight line on a plane opposed to the irradiating point when projected onto the plane, and the directions in which first and second light beams split from the measuring light beam in the other of the first optical interference systems impinge upon the irradiating point are directions which extend along a direction perpendicular to the straight line on said plane when projected onto the plane, and in this case, the distinguishing means determines the flow rate of blood and the flow direction of blood on the basis of the value of $fx^2 + fy^2$ wherein fx and fy represent the frequency deviations of the beat components generated by the respective first optical interference systems.

Also, the blood vessel distinguishing system should preferably be modified such that an additional first optical interference system having the same arrangement as said first optical interference system may be provided so that the directions in which first and second light beams split from the measuring light beam in one of the first optical interference systems impinge upon the irradiating point are directions which extend along a straight line on a plane opposed to the irradiating point when projected onto the plane, and the directions in which first and second light beams split from the measuring light beam in the other of the first optical interference systems impinge upon the irradiating point are directions which extend along a direction making an angle of θ, where 0°<θ<90°, with said straight line on said plane when projected onto the plane, and in this case, the distinguishing means determines the flow rate of blood and the flow direction of blood on the basis of the values of fx' and fy' wherein fx' and fy' represent the frequency deviations of the beat components generated by the respective first optical interference systems.

It is preferred that also the blood vessel distinguishing system in accordance with the third aspect of the present invention be provided with an in-phase time detecting means for detecting in-phase times, at which the flow rate of blood in the blood vessel to be distinguished becomes a predetermined value, and outputting a timing signal, and the distinguishing means samples a beat component detection signal at times, at which the flow rate of the blood is substantially maximized, and utilizes the sampled beat component detection signal for the blood vessel distinguishing.

The in-phase time detecting means may be, for instance, a means for detecting the pulse wave of the organism, or a means for detecting the times at which the frequency of the beat components generated by the first optical interference system takes a peak value.

In the aforesaid blood vessel imaging systems in accordance with the present invention, the characteristics are utilized in that the frequency deviation, which occurs when the measuring light beam impinges upon the blood vessel part, varies for the artery and the vein. In this manner, the artery is imaged by being distinguished from the vein. In the course of the imaging, the frequency deviation of the beat component detection signal (the beat signal) is calculated. Therefore, the artery and the vein can be distinguished from each other on the basis of the frequency deviation of the beat signal. With the technique described above, the blood vessel distinguishing system in accordance with the third aspect of the present invention distinguishes the blood vessels.

In accordance with a fourth aspect of the present invention, there is provided a frequency deviation measuring system comprising a measuring light source which emits a measuring light beam impinging upon a scattering fluid, a first optical interference system constituted such that a frequency of first beat components, which are generated by the measuring light beam and which are detected, changes in accordance with a flow rate of the scattering fluid due to a Doppler effect with the scattering fluid, a second optical interference system for causing signal light and a local oscillator beam, which has been modulated with a frequency different from the frequency of the first beat components detected by the first optical interference system, to interfere with each other, and thereby generating second beat components having a frequency different from the frequency of the first beat components, and a deviation measuring means for measuring a frequency deviation of a beat signal, which is formed by the second beat components, from the modulation frequency of the local oscillator beam.

As the first optical interference system described above, a system constituted of an optical homodyne interference system, a system constituted of an optical heterodyne interference system, or the like, is appropriate.

Also, the deviation measuring means should preferably be constituted so as to calculate the absolute value of the flow rate of the scattering fluid from the magnitude of the measured frequency deviation.

With the frequency deviation measuring system in accordance with the fourth aspect of the present invention, the aforesaid technique for calculating the frequency deviation is applied to the measurement of the frequency deviation with respect to scattering fluids, and the frequency deviation can be measured accurately

DESCRIPTION OF THE PREFERRED EMBODIMENTS

Figure 1:
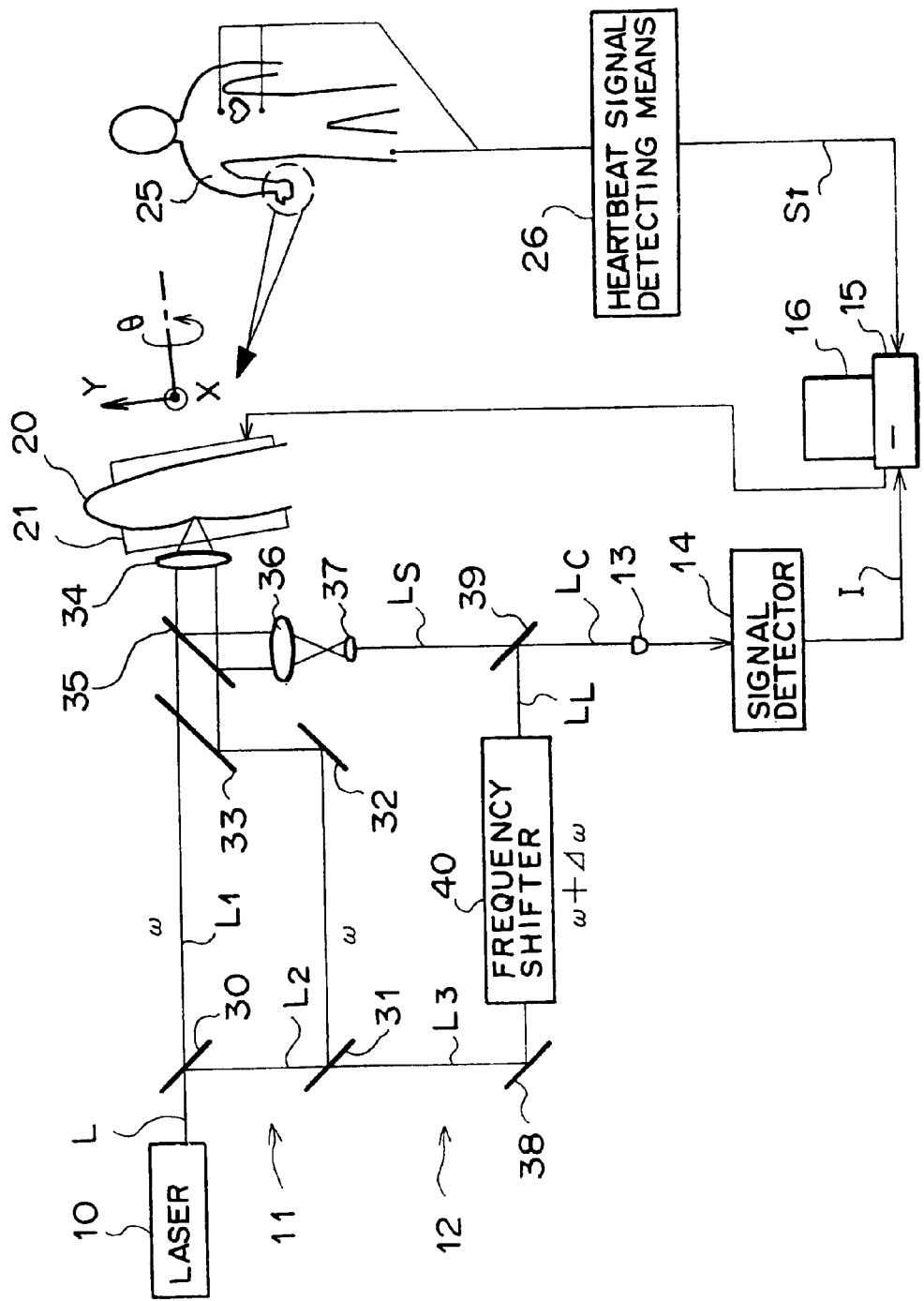
FIG. 1 is a schematic view showing a blood vessel imaging system in accordance with a-first embodiment of the present invention.

In FIG. 1, a blood vessel imaging system in accordance with a first embodiment of the present invention comprises a laser 10 emitting a measuring light beam L at a wavelength of $\lambda$ (a frequency of $\omega$), an optical homodyne interference system 11, an optical heterodyne interference system 12, a photodetector 13 which receives the measuring light beam L emanating from the optical heterodyne interference system 12, and a signal detector 14 connected to the photodetector 13. The imaging system further comprises a personal computer 15 which receives output of the signal detector 14 and forms an image signal generating means together with the signal detector 14, and an image monitor 16 such as a CRT display connected to the personal computer 15.

Further, there is provided a X-Y-$\theta$ stage 21 which is movable in X and Y directions and rotatable supporting thereon an object (e.g., a human finger) 20. The X-Y-$\theta$ stage 21 is driven under the control of the personal computer 15. Further, a heartbeat signal detecting means 26, which comprises an electrocardiograph for detecting heartbeat of the human 25 who is the possessor of the object 20, is connected to the personal computer 15.

The optical homodyne interference system 11 comprises a half-silvered mirror 30 which splits the measuring light beam L into a first light beam L1 and a second light beam L2, a half-silvered mirror 31 which splits a third light beam L3 from the second light beam L2, a mirror 32 which reflects the second light beam L2 reflected by the half-silvered mirror 31, a half-silvered mirror 33 which reflects the second light beam L2 reflected by the mirror 32 while transmitting the first light beam L1 passing through the half-silvered mirror so that the first and second light beams L1 and L2 travel in parallel to each other with their optical axes shifted from each other, a condenser lens 34 which converges the first and second light beams L1 and L2 inside the object 20, a half-silvered mirror 35 which reflects the first and second light beams L1 and L2 scattered by the object 20 to travel apart from the optical path of the first and second light beams L1 and L2 toward the object 20, and a pair of condenser lenses 36 and 37 which condense the scattered first and second light beams L1 and L2. The scattered first and second light beams L1 and L2 emanating from the condenser lens 37 form a signal light (combined scattered light beam) Ls to the optical heterodyne interference system 12.

The optical heterodyne interference system 12 comprises, in addition to said half-silvered mirrors 31 and 35 and said condenser lenses 36 and 37, a mirror 38 which reflects the third light beam L3 (a part of the second light beam L2 passing through the half-silvered mirror 31), and a half-silvered mirror 39 which combines the third light beam L3 reflected by the mirror 38 with the signal light $L_S$.

A frequency shifter 40 provided on the optical path of the third light beam L3 shifts the frequency of the third light beam L3 by a predetermined amount $\Delta\omega$ so that the center frequency of the third light beam L3 becomes $\omega+\Delta\omega$. The frequency shifter 40 may comprise, for instance, an AOM. The frequency-shifted third light beam L3 forms a local oscillator beam $L_L$ of the optical heterodyne interference system 12.

Operation of the blood vessel imaging system of this embodiment will be described, hereinbelow. When taking a blood vessel image, a measuring light beam L is emitted from the laser 10 and the first and second light beams L1 and L2 are projected onto the object 20. While projecting the first and second light beams L1 and L2, the X-Y-θ stage 21 is moved in X and Y directions, whereby the first and second light beams L1 and L2 are caused to two-dimensionally scan the object 20. At this time, since the first and second light beams L1 and L2 travel in parallel to each other with their optical axes shifted from each other, the first and second light beams L1 and L2 impinge upon an irradiating point P on the object 20 in different directions as shown in FIG. 2.

Figure 2:
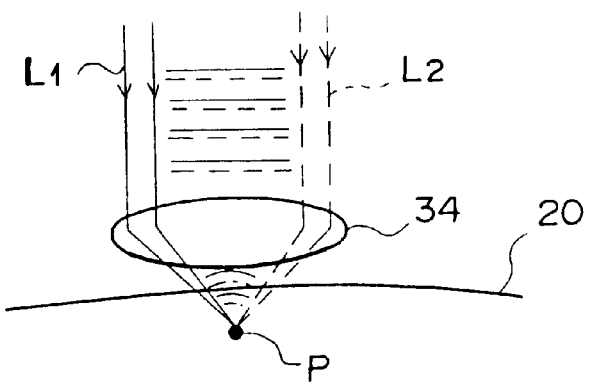
FIG. 2 is a view showing a part of the optical path of the measuring light beam in the blood vessel imaging system of the first embodiment.

As shown in FIG. 2, the first light beam L1 impinges upon the irradiating point P along the optical path shown by the solid line and the first light beam L1 scattered and reflected by the object 20 is condensed by the condenser lens 34 to travel away from the object 20 along the optical axis of the condenser lens 34. Whereas, the second light beam L2 impinges upon the irradiating point P along the optical path shown by the broken line and the second light beam L2 scattered and reflected by the object 20 is condensed by the condenser lens 34 to travel away from the object 20 along the optical axis of the condenser lens 34.

When the irradiating point P is on a blood vessel part, the frequencies of the scattered first and second light beams L1 and L2 are deviated by Doppler effect due to a flow of blood in the blood vessel part. Assuming that the amount of frequency deviation of one of the first and second light beams L1 and L2 is $\Delta f$, the amount of frequency deviation of the other of the first and second light beams L1 and L2 is $-\Delta f$. The frequency deviations of the first and second light beams L1 and L2 generate beat signals at a frequency of $2\Delta f$ in the combined scattered light beam (the signal light $L_S$) by interference.

The signal light $L_S$ including therein the beat components generated by the optical homodyne interference system 11 is combined with the frequency-shifted third light beam L3 (the local oscillator beam $L_L$ whose center frequency is $\omega+\Delta\omega$) by the half-silvered mirror 39 into a combined light beam $L_c$.

Beat components whose center frequency is $\Delta\omega$ are generated by interference in the combined light beam Lc. The beat components are superimposed on the aforesaid beat components at frequency $2\Delta f$ and accordingly the amplitude of the beat components at frequency $2\Delta f$ is theoretically amplified to $(A2/A1)^{1/2}$ times wherein A1 represents the amplitude of the beat signal by the optical interference system and A2 represents the amplitude of the beat signal by the heterodyne detection system.

The output of the photodetector 13 upon receipt of the combined light beam Lc includes a beat signal I generated by the beat components at frequency $2\Delta f$. The output of the photodetector 13 is input into the signal detector 14. The signal detector 14 may comprise, for instance, a band-pass filter and a level meter, and extracts the beat signal I and inputs it into the personal computer 15.

Figure 3:
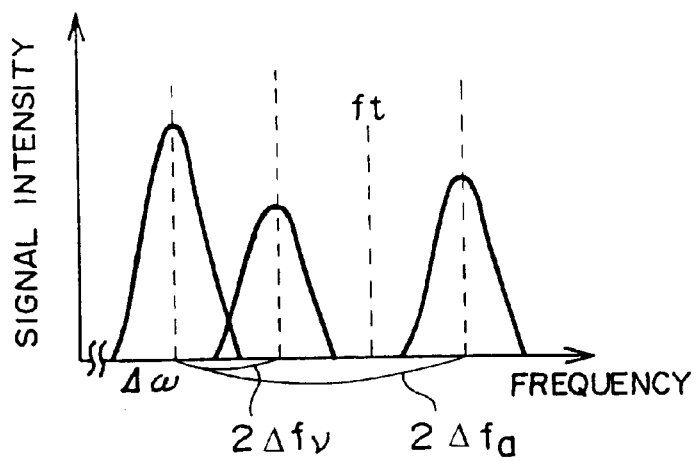
FIG. 3 is a schematic view showing the relation between the intensity of the beat signal and the threshold value in the blood vessel imaging system.

The personal computer 15 sets a threshold value ft such as shown in FIG. 3 with respect to the frequency $2\Delta f$ of the beat signal I, and generates an image signal component bearing thereon a relatively high density (low brightness) when the frequency $2\Delta f$ is higher than the threshold value ft and otherwise an image signal component bearing thereon a relatively low density (high brightness). The personal computer 15 inputs the image signal component into the monitor 16.

As described above, the frequency deviation $\Delta f$ by the optical homodyne interference system 11 is in proportion to the flow rate of the fluid and the flow rate of blood is higher in arteries than in veins. Accordingly, the frequency deviation $\Delta fa$ when the measuring light beam L (the first and second light beams L1 and L2) is projected onto an artery is larger than the frequency deviation $\Delta fv$ when the measuring light beam L is projected onto a vein. As shown in FIG. 3, the threshold value ft is set between the frequencies $2\Delta fa$ and $2\Delta fv$ which are empirically determined. Accordingly, the image signal bearing thereon a relatively high density generated by the personal computer 15 in the manner described represents a picture element of an artery part.

The personal computer 15 generates an image signal component for each scanning spot on the object 20 as the first and second light beams L1 and L2 scan the object 20. The image monitor 16 reproduces a two-dimensional image on the basis of an image signal made up of the image signal components thus generated for the respective scanning spots. In the image, only the artery part of the object 20 is shown at a relatively high density.

When the personal computer 15 generates an image signal component bearing thereon a relatively high density (low brightness) when the frequency $2\Delta f$ is not higher than the threshold value ft and otherwise an image signal component bearing thereon a relatively low density (high brightness)

and inputs the image signal component into the monitor 16, an image in which only the vein part of the object 20 is shown at a relatively high density can be obtained.

Since the measuring light beam L scattered by a blood vessel is inherently very weak, the beat signal I is also very weak. However, in the blood vessel imaging system of this embodiment, the amplitude of the beat signal I is amplified by the heterodyne detection system as described above. Accordingly, the beat signal I can be detected at a high S/N ratio, whereby even a peripheral artery or the like deep in the hand or foot can be clearly imaged.

The X-Y-θ stage 21 is rotatable in the direction of θ about an axis extending substantially left to right in FIG. 1 as well as movable in X- and Y-directions. Rotation of X-Y-θ stage 21 will be described with reference to also FIGS. 4A to 4C, hereinbelow.

Figure 4A:
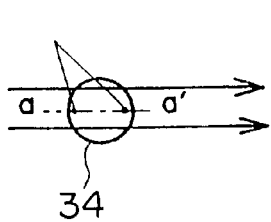
FIGS. 4A to 4C are views showing the relations between the directions of incidence of the first and second light beams and the direction of flow of blood.
Figure 4B:
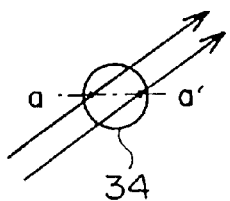
Figure 4C:
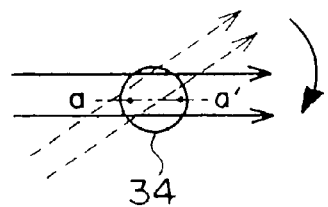

FIGS. 4A to 4C are views showing the relations between the directions of incidence of the first and second light beams L1 and L2 and the direction of flow of blood. In FIGS. 4A to 4C, arrows indicate the direction of flow of blood. The amplitude of the beat signal generated by the optical homodyne interference system 11 is maximized when the direction of flow of blood is parallel to straight line a–a' which joins the beam exit points (shown by black dots) on the surface of the condenser lens 34 at which the first and second light beams L1 and L2 exit the lens 34 as shown in FIG. 4A. Accordingly, when the direction of flow of blood is not parallel to the straight line a–a' as shown in FIG. 4B, the direction of flow of blood can be made parallel to the straight line a–a' as shown in FIG. 4C by rotating the X-Y-θ stage 21, whereby the beat signal I can be detected at a higher S/N ratio.

When rotating the X-Y-θ stage 21 for this purpose, it is not necessary to watch the directions of incidence and the direction of the flow of blood but the X-Y-θ stage 21 has only to be operated monitoring the beat signal I so that the intensity of the beat signal I is maximized.

Figure 5:
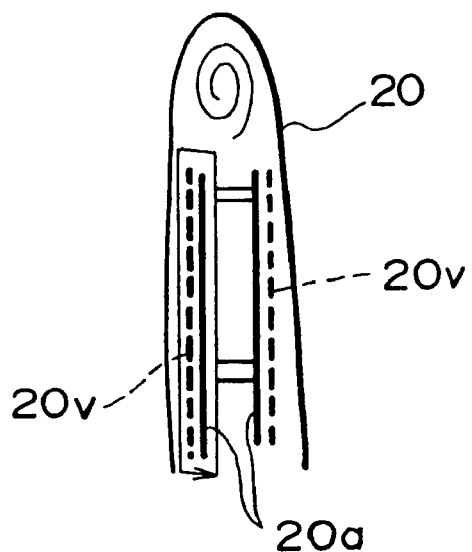
FIG. 5 is a side view of the object.

However in the case where the object 20 is a finger or the like and the direction in which the blood vessel to be imaged extends can be easily known, it is not necessary that the positions of the optical homodyne interference system 11 and the object 20 relative to each other is adjustable. That is, it has been known that arteries 20a in the finger (the object 20) extends substantially in the longitudinal direction of the finger as shown in FIG. 5, and accordingly, the intensity of the beat signal I is maximized by simply positioning the finger in parallel to the aforesaid straight line a–a'. Reference numeral 20v in FIG. 5 denotes a vein.

The flow rate of arterial blood varies with pulsation and sometimes becomes very close to that of the venous blood. Accordingly, when the beat components are detected at the minimum flow rate of arterial blood, an artery and a vein sometimes cannot be clearly distinguished from each other.

The heartbeat signal detecting means 26 is provided for overcoming this problem. That is, the heartbeat signal detecting means 26 monitors the output waveform of an electrocardiograph shown by line Hb in FIG. 6 and inputs a timing signal St (FIG. 1) into the personal computer 15. The personal computer 15 samples the beat signal I a predetermined time after receipt of the timing signal St and generates an image signal component on the basis of the sampled beat signal I.

Figure 6:
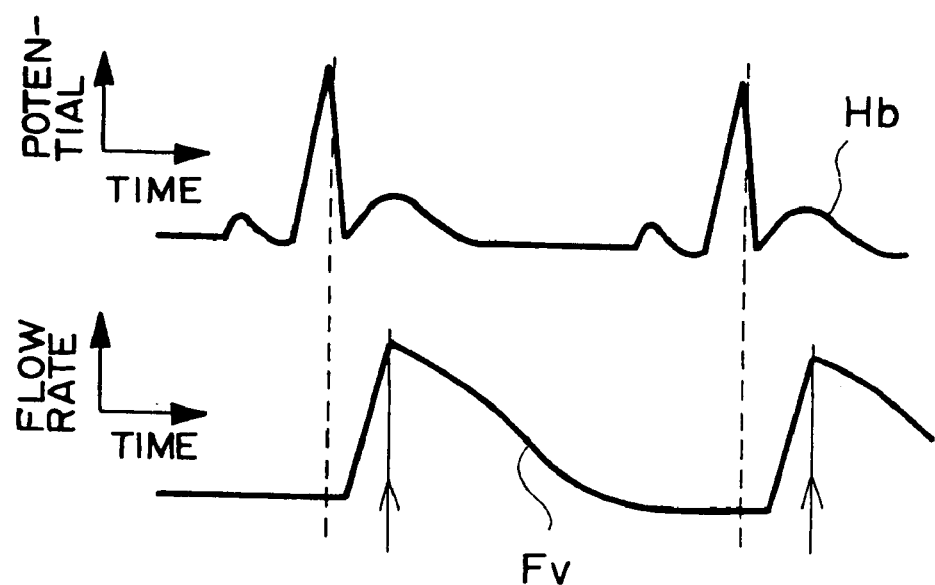
FIG. 6 is a view showing the change with time of the output of the electrocardiograph and the flow rate of arterial blood.

Line Fv in FIG. 6 shows the variation of the flow rate of arterial blood. As can be seen from comparison of line Hb and line Fv, the flow rate of arterial blood is maximized a predetermined time after the output of the electrocardiograph is maximized. Accordingly, when the beat signal I is sampled on the basis of the timing signal St in the manner described above, an image signal component can be constantly generated on the basis of a value of the beat signal I at a time the flow rate of arterial blood is substantially maximized, whereby the aforesaid problem can be avoided.

Figure 7:
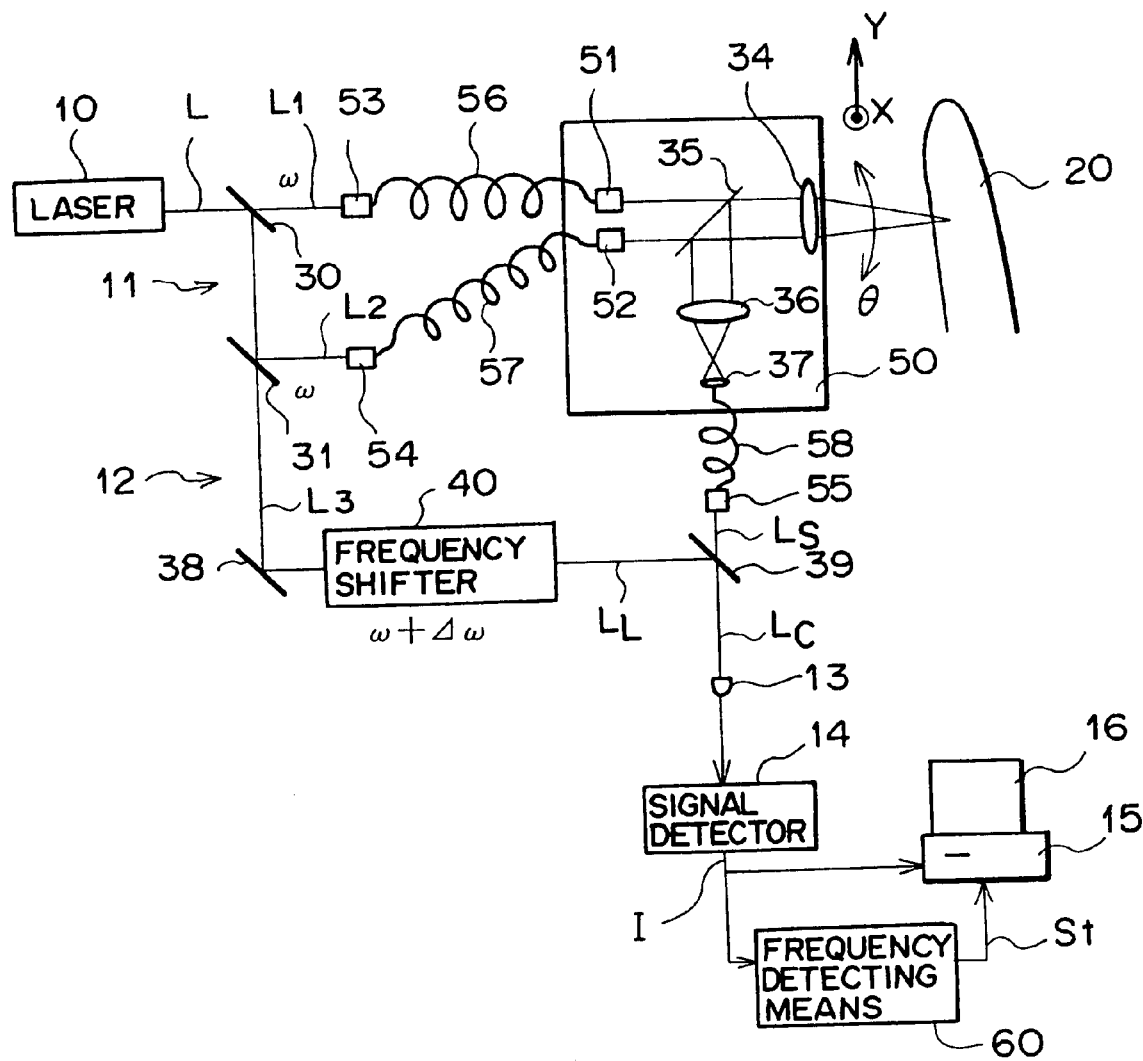
FIG. 7 is a schematic view showing a blood vessel imaging system in accordance with a second embodiment of the present invention.

A blood vessel imaging system in accordance with a second embodiment of the present invention will be described with reference to FIG. 7, hereinbelow. In FIG. 7, the elements analogous to those shown in FIG. 1 are given the same reference numerals and will not be described here.

In the blood vessel imaging system of this embodiment, a pickup 50 which is two-dimensionally movable and rotatable like the X-Y-θ stage 21 in the first embodiment is provided. The condenser lens 34, the half-silvered mirror 35 and the condenser lenses 36 and 37 are mounted on the pickup 50. A pair of rod lenses 51 and 52 are fixed to the pickup 50 to be opposed to different positions of the condenser lens 34 with the half-silvered mirror 35 intervening between the condenser lens 34 and the rod lenses 51 and 52.

Outside the pickup 50, a rod lens 53 is disposed to receive the first light beam L1 passing through the half-silvered mirror 30, a rod lens 54 is disposed to receive the second light beam L2 reflected by the half-silvered mirror 31 and a rod lens 55 is opposed to the photodetector 13 with the half-silvered mirror 39 intervening therebetween.

The rod lens 53 is optically connected to the rod lens 51 by way of an optical fiber 56. The first light beam L1 passing through the half-silvered mirror 30 is condensed by the rod lens 53 and enters the optical fiber 56. Then the first light beam L1 propagates through the optical fiber 56, exits from the rod lens 51 and impinges upon an irradiating point on the object 20 through the condenser lens 34. The rod lens 54 is optically connected to the rod lens 52 by way of an optical fiber 57. The second light beam L2 reflected by the half-silvered mirror 31 is condensed by the rod lens 54 and enters the optical fiber 57. Then the second light beam L2 propagates through the optical fiber 57, exits from the rod lens 52 and impinges upon the same irradiating point on the object 20 through the condenser lens 34.

The rod lens 55 is connected to the condenser lens 37 by way of an optical fiber 58. The scattered first and second light beams L1 and L2 (the signal light beam $L_s$) scattered by the object 20 and the half-silvered mirror 35 and condensed by the condenser lenses 36 and 37 propagates through the optical fiber 58 and exits.from the rod lens 55 to impinge upon the photodetector 13.

In this embodiment, since the optical elements mounted on the pickup 50 and those outside the pickup 50 are connected through the flexible optical fibers, the first and second light beams L1 and L2 can be caused to two-dimensionally scan the object 20 by moving the pickup 50 and the directions of incidence of the first and second light beams L1 and L2 relative to the direction of flow of blood can be optimized by rotating the pickup 50.

Further in the blood vessel imaging system of this embodiment, a frequency detecting means 60 is provided as an in-phase time detecting means in place of the heartbeat signal detecting means 26 in the first embodiment. The frequency detecting means 60 monitors the beat signal I output from the signal detector 14 and inputs a timing signal St at a time the frequency of the beat signal I is maximized. The personal computer 15 samples the beat signal I upon receipt of the timing signal St and generates an image signal component on the basis of the sampled beat signal I.

Thus also in this embodiment, an image signal component can be constantly generated on the basis of a value of the beat signal I at a time the flow rate of arterial blood is substantially maximized, whereby an artery and a vein can be clearly distinguished from each other.

An blood vessel imaging system in accordance with a third embodiment of the present invention will be described with reference to FIG. 8, hereinbelow.

Figure 8:
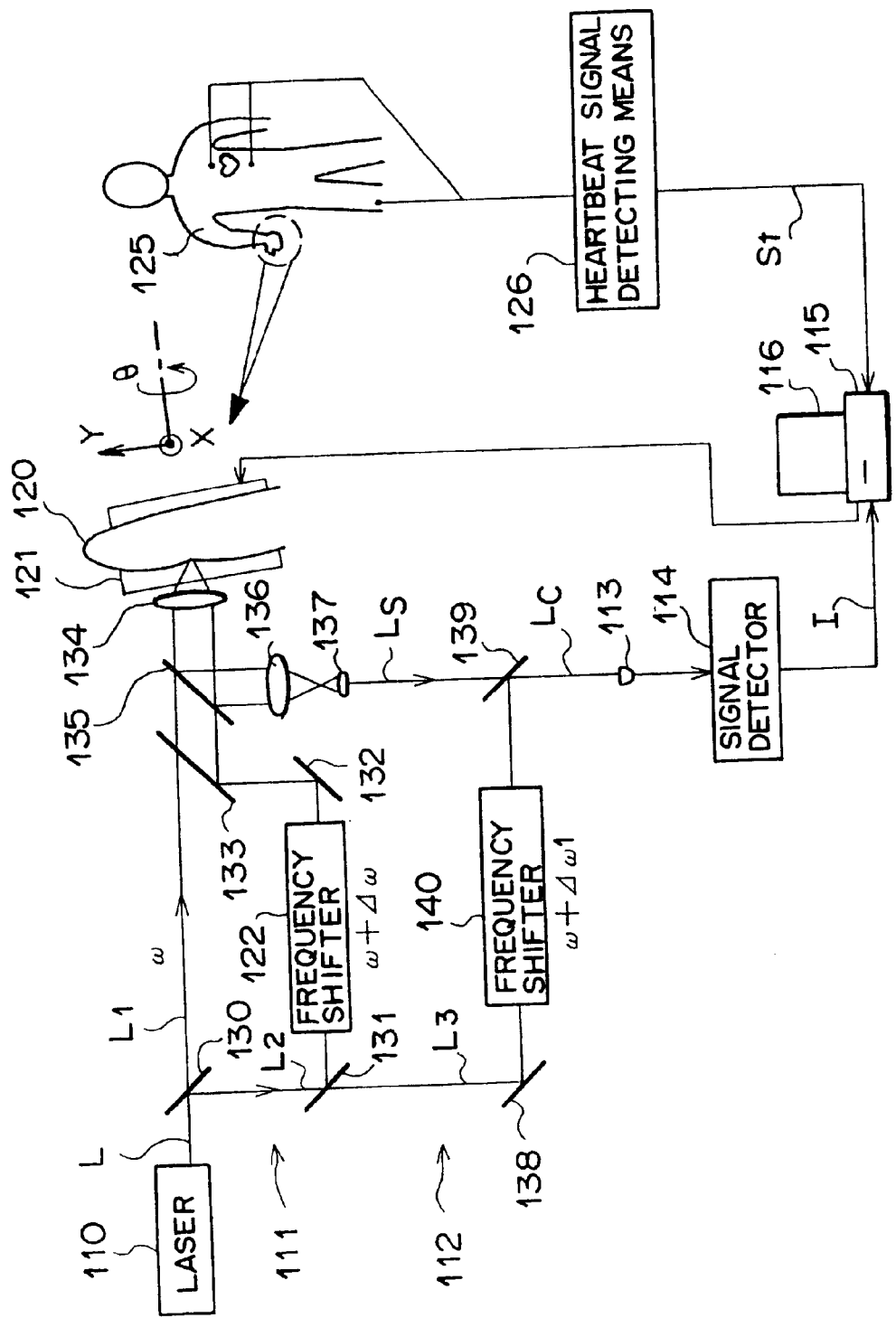
FIG. 8 is a schematic view showing a blood vessel imaging system in accordance with a third embodiment of the present invention.

In FIG. 8, a blood vessel imaging system in accordance with a third embodiment of the present invention comprises a laser 110 emitting a measuring light beam L at a wavelength of λ (a frequency of ω), a first optical system 111 which forms an optical interference system, a second optical system 112 which forms an optical heterodyne detection system, a photodetector 113 which receives the measuring light beam L emanating from the second optical system 112, and a signal detector 114 connected to the photodetector 113. The imaging system further comprises a personal computer 115 which receives output of the signal detector 114 and forms an image signal generating means together with the signal detector 114, and an image monitor 116 such as a CRT display connected to the personal computer 115.

Further, there is provided a X-Y-θ stage 121 which is movable in X and Y directions and rotatable supporting thereon an object (e.g., a human finger) 120. The X-Y-θ stage 121 is driven under the control of the personal computer 115. Further, a heartbeat signal detecting means 126, which comprises an electrocardiograph for detecting heartbeat of the human 125 who is the possessor of the object 120, is connected to the personal computer 115.

The first optical system 111 comprises a half-silvered mirror 130 which splits the measuring light beam L into a first light beam L1 and a second light beam L2, a half-silvered mirror 131 which splits a third light beam L3 from the second light beam L2, a mirror 132 which reflects the second light beam L2 reflected by the half-silvered mirror 131, a half-silvered mirror 133 which reflects the second light beam L2 reflected by the mirror 132 while transmitting the first light beam L1 passing through the half-silvered mirror 130 so that the first and second light beams L1 and L2 travel in parallel to each other with their optical axes shifted from each other, a condenser lens 134 which converges the first and second light beams L1 and L2 inside the object 120, a half-silvered mirror 135 which reflects the first and second light beams L1 and L2 scattered by the object 120 to travel apart from the optical path of the first and second light beams L1 and L2 toward the object 120, and a pair of condenser lenses 136 and 137 which condense the scattered first and second light beams L1 and L2 into a combined scattered beam $L_S$.

A first frequency shifter 122 provided on the optical path of the second light beam L2 shifts the frequency of the second light beam L2 by a predetermined amount Δω so that the center frequency of the second light beam L2 becomes ω+Δω. The first frequency shifter 122 may comprise, for instance, an AOM.

The second optical system 112 comprises, in addition to said half-silvered mirrors 131 and 135 and said condenser lenses 136 and 137, a mirror 138 which reflects the third light beam L3 (a part of the second light beam L2 passing through the half-silvered mirror 131), and a half-silvered mirror 139 which combines the third light beam L3 reflected by the mirror 138 with the combined scattered beam $L_S$ condensed by the condenser mirrors 136 and 137.

A second frequency shifter 140 provided on the optical path of the third light beam L3 shifts the frequency of the third light beam L3 by a predetermined amount Δω1 so that the center frequency of the third light beam L3 becomes ω+Δω1. The frequency shifter 140 may comprise, for instance, an AOM. Operation of the blood vessel imaging system of this embodiment will be described, hereinbelow. When taking a blood vessel image, a measuring light beam L is emitted from the laser 110 and the first and second light beams L1 and L2 are projected onto the object 120. While projecting the first and second light beams L1 and L2, the X-Y-θ stage 121 is moved in X- and Y-directions, whereby the first and second light beams L1 and L2 are caused to two-dimensionally scan the object 120. At this time, since the first and second light beams L1 and L2 travel in parallel to each other with their optical axes shifted from each other, the first and second light beams L1 and L2 impinge upon an irradiating point P on the object 120 in different directions as shown in FIG. 9.

Figure 9:
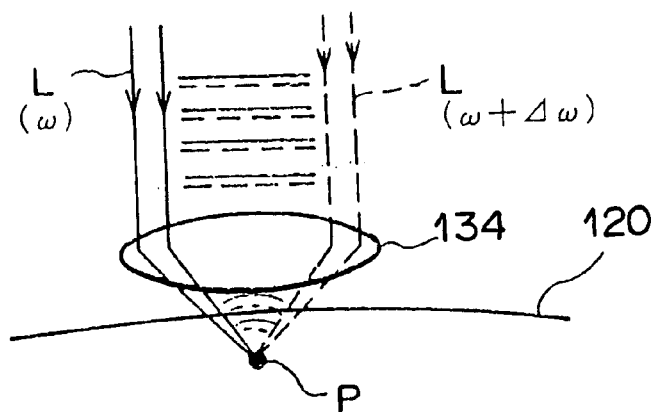
FIG. 9 is a view showing a part of the optical path of the measuring light beam in the blood vessel imaging system of the third embodiment.

As shown in FIG. 9, the first light beam L1 at the frequency ω impinges upon the irradiating point P along the optical path shown by the solid line and the first light beam L1 scattered and reflected by the object 120 is condensed by the condenser lens 134 to travel away from the object 120 along the optical axis of the condenser lens 34. Whereas, the second light beam L2 at the frequency (ω+Δω) impinges upon the irradiating point P along the optical path shown by the broken line and the second light beam L2 scattered and reflected by the object 120 is condensed by the condenser lens 134 to travel away from the object 120 along the optical axis of the condenser lens 134.

The scattered first and second light beams L1 and L2 into a combined scattered light beam $L_S$ as described above. When no blood flow exists on the irradiating point P, beat signal components at a frequency Δω are generated in the combined scattered light beam $L_S$. Whereas, when a blood flow exists on the irradiating point P, the frequencies of the scattered first and second light beams L1 and L2 are deviated by Doppler effect due to the flow of blood. Assuming that the frequency of the scattered second light beam L2 is ω+Δω+fa (fa being the frequency deviation) when the irradiating point P is on an artery part, the frequency of the scattered first light beam L1 is ω−fa. Accordingly when the scattered first and second light beams L1 and L2 are combined into a combined scattered light beam $L_S$, beat components at a frequency +Δω+fa−(ω−fa)=Δω+2fa are generated in the combined scattered light beam $L_S$ by interference.

On the other hand, when the irradiating point P is on a vein part, the flow of blood in the vein is opposite to that in the artery in the finger and accordingly, when the frequency deviation at that time is represented by fv, beat components at a frequency ω+Δω−fv−(ω+fv)=Δω−2fv are generated in the combined scattered light beam $L_S$ by interference.

The combined scattered light beam $L_S$ including therein the beat components generated by the first optical interference system 111 is combined with the frequency-shifted third light beam L3 by the half-silvered mirror 139 into a combined light beam $L_c$.

Beat components whose center frequency is Δω1 are generated by interference in the combined light beam $L_c$ by interference between the frequency-shifted third light beam L3 from the second frequency shifter 140 and the combined scattered light beam $L_s$ from the condenser lenses 136 and 137. The beat components are superimposed on the aforesaid beat components at frequency (Δω+2fa) or (Δω−2fv) and accordingly the amplitude of the beat components at frequency (Δω+2fa) or (Δω−2fv) is theoretically amplified to $(A2/A1)^{1/2}$ times wherein A1 represents the amplitude of the beat signal by the optical interference system formed by the first optical system 111 and A2 represents the amplitude of the beat signal by the optical heterodyne detection system formed by the second optical system 112.

The combined light beam $L_C$ is photoelectrically detected by the photodetector 113. The output of the photodetector 113 upon receipt of the combined light beam $L_c$ after all makes a beat signal I at a frequency ($\Delta\omega-\Delta\omega1+2fa$) or ($\Delta\omega-\Delta\omega1-2fv$). The output of the photodetector 113 is input into the signal detector 114. The signal detector 114 may comprise, for instance, a band-pass filter and a level meter, and extracts the beat signal I and inputs it into the personal computer 115.

Figure 10:
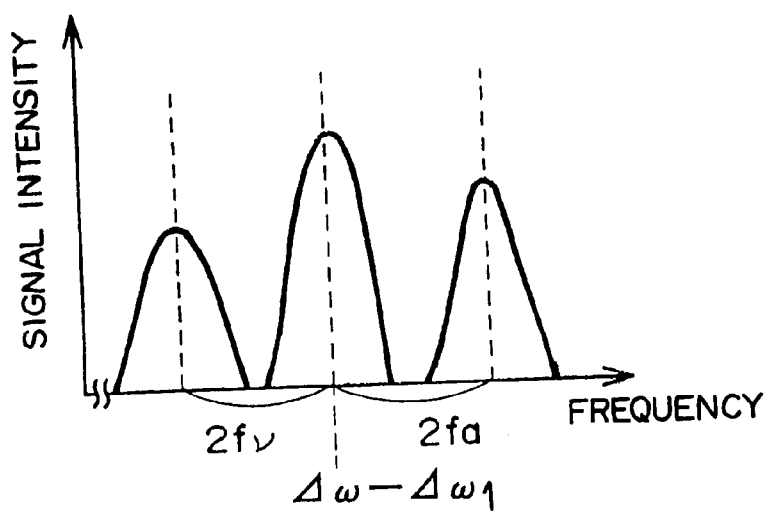
FIG. 10 is a schematic view showing the relation between the intensity of the beat signal and the threshold value in the blood vessel imaging system.

The personal computer 115 sets a threshold value ($\Delta\omega-\Delta\omega1$) as shown in FIG. 10 with respect to the frequency ($\Delta\omega-\Delta\omega1+2fa$) or ($\Delta\omega-\Delta\omega1-2fv$) of the beat signal I, and generates an image signal component bearing thereon a relatively high density (low brightness) when the frequency of the beat signal I is higher than the threshold value ($\Delta\omega-\Delta\omega1$) and otherwise an image signal component bearing thereon a relatively low density (high brightness). The personal computer 115 inputs the image signal component into the monitor 116. The image signal component bearing thereon a relatively high density generated by the personal computer 115 in the manner described represents a picture element of an artery part.

The personal computer 115 generates an image signal component for each scanning spot on the object 120 as the first and second light beams L1 and L2 scan the object 120. The image monitor 116 reproduces a two-dimensional image on the basis of an image signal made up of the image signal components thus generated for the respective scanning spots. In the image, only the artery part of the object 120 is shown at a relatively high density.

When the personal computer 115 generates an image signal component bearing thereon a relatively high density (low brightness) when the frequency of the beat signal I is not higher than the threshold value ($\Delta\omega-\Delta\omega1$) and otherwise an image signal component bearing thereon a relatively low density (high brightness) and inputs the image signal component into the monitor 116, an image in which only the vein part of the object 120 is shown at a relatively high density can be obtained.

Since the measuring light beam L scattered by a blood vessel is inherently very weak, the beat signal I is also very weak. However, in the blood vessel imaging system of this embodiment, the amplitude of the beat signal I is amplified by the heterodyne detection system formed by the second optical system 112, the second frequency shifter 140 and the photodetector 113 as described above. Accordingly, the beat signal I can be detected at a high S/N ratio, whereby even a peripheral artery or the like deep in the hand or foot can be clearly imaged.

The X-Y-θ stage 121 is rotatable in the direction of θ about an axis extending substantially left to right in FIG. 8 as well as movable in X- and Y-directions. Operation of the X-Y-θ stage 121 and the heartbeat signal detecting means 126 are the same as that of the X-Y-θ stage 21 and the heartbeat signal detecting means 26 in the first embodiment, and accordingly will not be described here.

Figure 11:
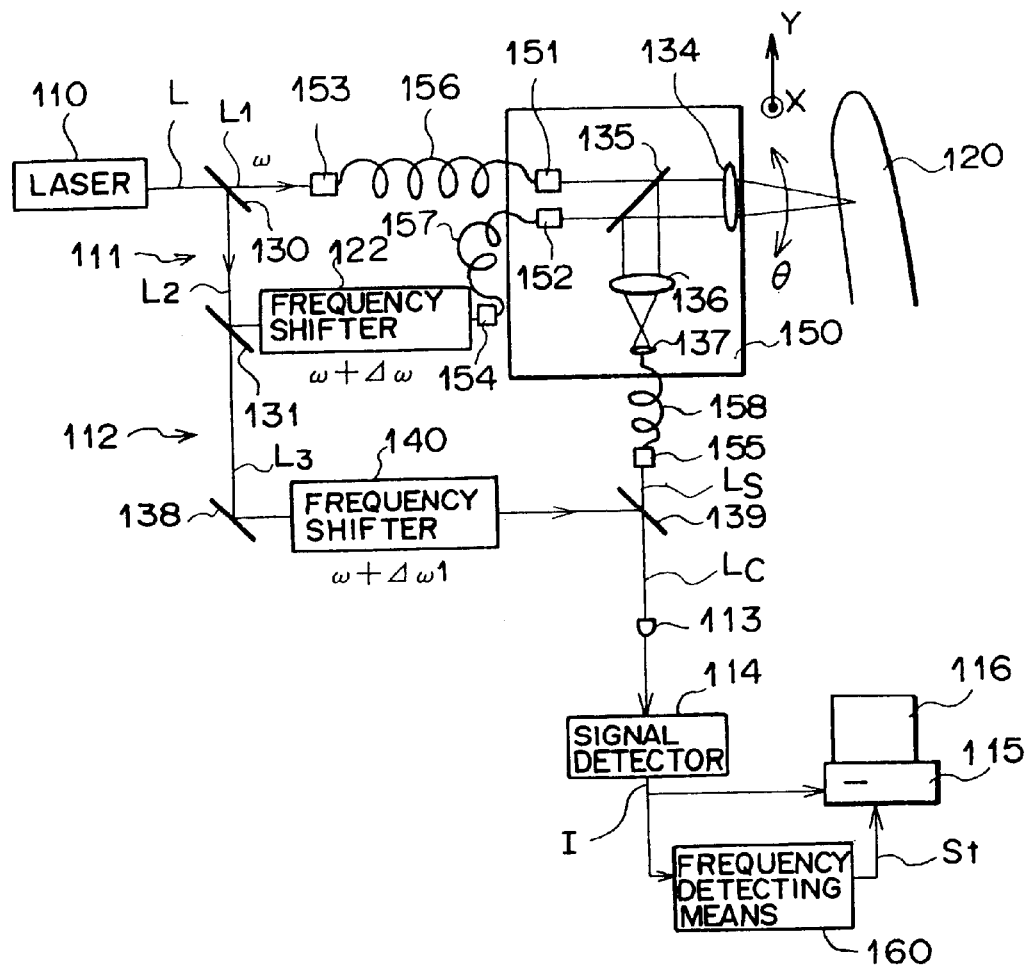
FIG. 11 is a schematic view showing a blood vessel imaging system in accordance with a fourth embodiment of the present invention.

A blood vessel imaging system in accordance with a fourth embodiment of the present invention will be described with reference to FIG. 11, hereinbelow. In FIG. 11, the elements analogous to those shown in FIG. 8 are given the same reference numerals and will not be described here.

In the blood vessel imaging system of this embodiment, a pickup 150 which is two-dimensionally movable and rotatable like the X-Y-θ stage 21 in the third embodiment is provided. The condenser lens 134, the half-silvered mirror 135 and the condenser lenses 136 and 137 are mounted on the pickup 150. A pair of rod lenses 151 and 152 are fixed to the pickup 150 to be opposed to different positions of the condenser lens 134 with the half-silvered mirror 135 intervening between the condenser lens 134 and the rod lenses 151 and 152.

Outside the pickup 150, a rod lens 153 is disposed to receive the first light beam L1 passing through the half-silvered mirror 130, a rod lens 154 is disposed to receive the second light beam L2 reflected by the half-silvered mirror 131 and a rod lens 155 is opposed to the photodetector 113 with the half-silvered mirror 139 intervening therebetween.

The rod lens 153 is optically connected to the rod lens 151 by way of an optical fiber 156. The first light beam L1 passing through the half-silvered mirror 130 is condensed by the rod lens 153 and enters the optical fiber 156. Then the first light beam L1 propagates through the optical fiber 156, exits from the rod lens 151 and impinges upon an irradiating point on the object 120 through the condenser lens 134. The rod lens 154 is optically connected to the rod lens 152 by way of an optical fiber 157. The second light beam L2 reflected by the half-silvered mirror 131 is condensed by the rod lens 154 and enters the optical fiber 157. Then the second light beam L2 propagates through the optical fiber 157, exits from the rod lens 152 and impinges upon the same irradiating point on the object 120 through the condenser lens 134.

The rod lens 155 is connected to the condenser lens 137 by way of an optical fiber 158. The scattered first and second light beams L1 and L2 (the combined scattered light beam $L_S$) scattered by the object 120 and the half-silvered mirror 135 and condensed by the condenser lenses 136 and 137 propagates through the optical fiber 158 and exits from the rod lens 155 to impinge upon the photodetector 113.

In this embodiment, since the optical elements mounted on the pickup 150 and those outside the pickup 150 are connected through the flexible optical fibers, the first and second light beams L1 and L2 can be caused to two-dimensionally scan the object 120 by moving the pickup 150 and the directions of incidence of the first and second light beams L1 and L2 relative to the direction of flow of blood can be optimized by rotating the pickup 150.

Further in the blood vessel imaging system of this embodiment, a frequency detecting means 160 is provided as an in-phase time detecting means in place of the heartbeat signal detecting means 126 in the third embodiment. The frequency detecting means 160 monitors the beat signal I output from the signal detector 114 and inputs a timing signal St at a time the frequency of the beat signal I is maximized. The personal computer 115 samples the beat signal I upon receipt of the timing signal St and generates an image signal component on the basis of the sampled beat signal I.

Thus also in this embodiment, an image signal component can be constantly generated on the basis of a value of the beat signal I at a time the flow rate of arterial blood is substantially maximized, whereby an artery and a vein can be clearly distinguished from each other.

Figure 12:
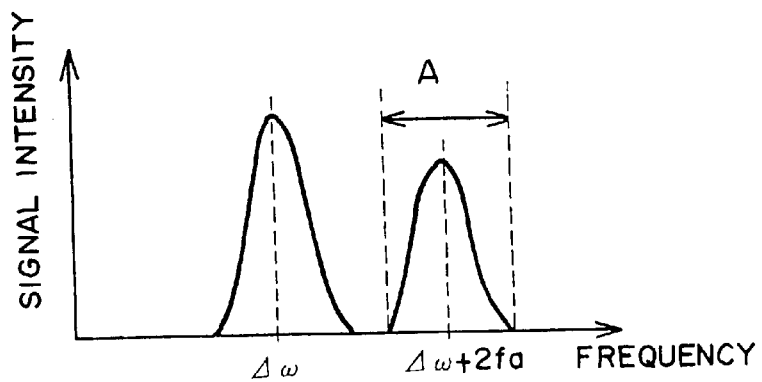
FIG. 12 is a view for illustrating change in the beat signal frequency according to the position in which the measuring light beam is projected.

As can be understood from the description above, when the measuring light beam L (the first and second light beams L1 and L2) scans the object 120 across an artery, the frequency of the beat signal I is $\Delta\omega$ when the irradiation point P is out of alignment with the artery and, when the irradiating point P is at least partly aligned with the artery, the frequency of the beat signal I takes a value in the range A shown in FIG. 12 according to how the irradiating point P is aligned with the artery, e.g., the irradiating point P is partly aligned with an edge of the artery, or aligned with the center of the same. Accordingly, when the measuring light beam L is caused to scan the object 120 in a direction transverse to the artery, and to reverse when the frequency of the beat signal I is gradually lowered from ($\Delta\omega$+2fa) and reaches $\Delta\omega$, the measuring light beam L can be prevented from scanning in vain a part other than the artery and only the artery part can be imaged.

Figure 13:
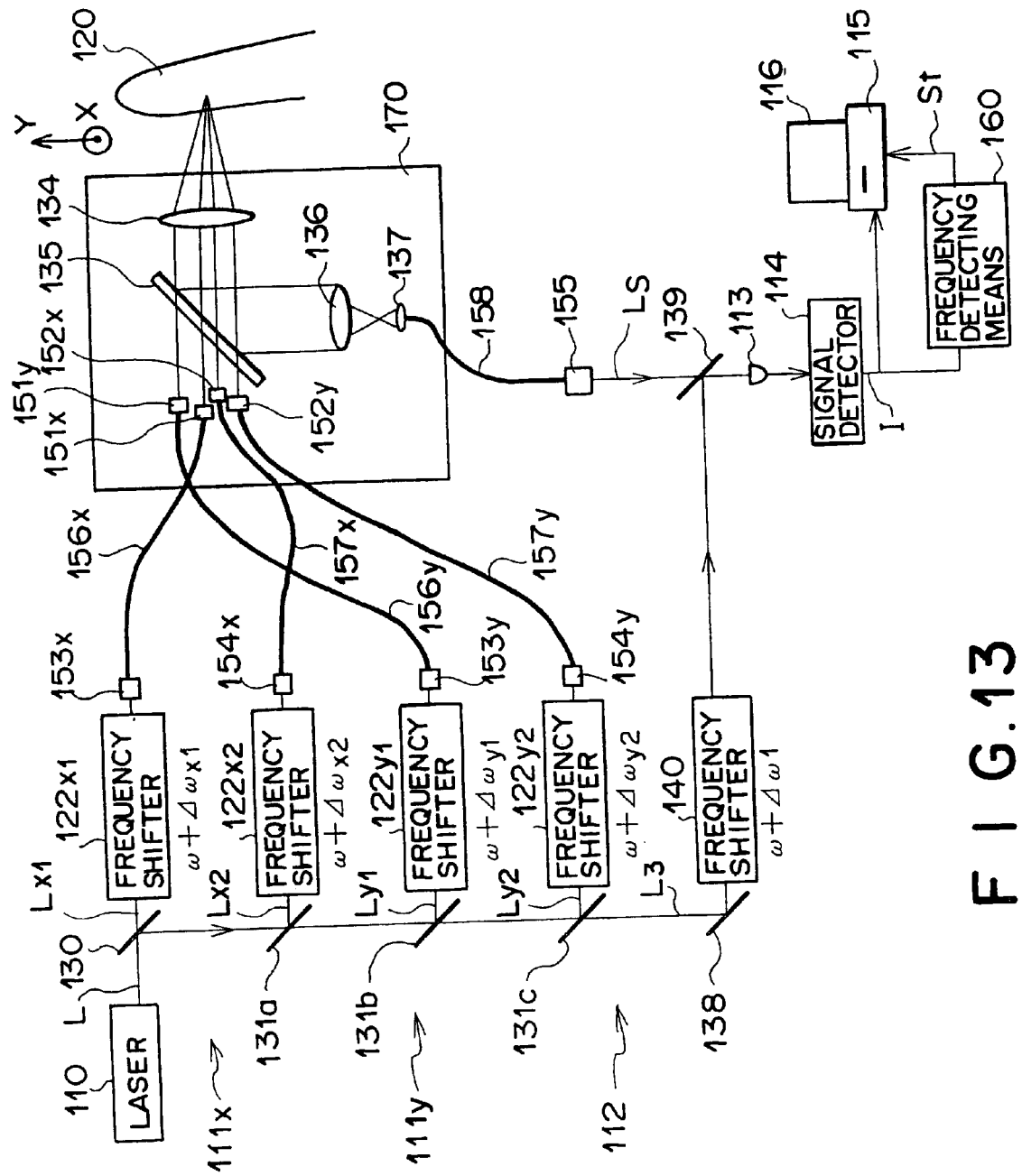
FIG. 13 is a schematic view showing a blood vessel imaging system in accordance with a fifth embodiment of the present invention.

A blood vessel imaging system in accordance with a fifth embodiment of the present invention will be described with reference to FIG. 13, hereinbelow. In FIG. 13, the elements analogous to those shown in FIG. 11 are given the same reference numerals and will not be described here. The blood vessel imaging system of this embodiment basically differs from that of the fourth embodiment in that a pair of first optical systems 111x and 111y are provided and a pickup 170 which is movable only in X- and Y-directions and is not rotatable is provided in place of the pickup 150 which is movable in X- and Y-directions and is rotatable.

The condenser lens 134, the half-silvered mirror 135 and the condenser lenses 136 and 137 are mounted on the pickup 170. Further, rod lenses 151x, 151y, 152x and 152y are fixed to the pickup 170 to be opposed to different positions of the condenser lens 134 with the half-silvered mirror 135 intervening between the condenser lens 134 and the rod lenses.

Outside the pickup 170, three half-silvered mirrors 131a, 131b and 131c are disposed between the half-silvered mirror 130 and the mirror 138, a rod lens 153x is disposed to receive a first light beam Lx1 of the first optical system 111x passing through the half-silvered mirror 130, a rod lens 154x is disposed to receive a second light beam Lx2 of the first optical system 111x reflected by the half-silvered mirror 131a, a rod lens 153y is disposed to receive a first light beam Ly1 of the first optical system 111y reflected by the half-silvered mirror 131b, a rod lens 154y is disposed to receive a second light beam Ly2 of the first optical system 111y reflected by the half-silvered mirror 131c, and a rod lens 155 is opposed to the photodetector 113 with the half-silvered mirror 139 intervening therebetween.

A frequency shifter 122x1 provided on the optical path of the first light beam Lx1 shifts the frequency of the first light beam Lx1 by a predetermined amount $\Delta\omega x1$ so that the center frequency of the first light beam Lx1 becomes $\omega+\Delta\omega x1$. A frequency shifter 122x2 provided on the optical path of the second light beam Lx2 shifts the frequency of the second light beam Lx2 by a predetermined amount $\Delta\omega x2$ so that the center frequency of the second light beam Lx2 becomes $\omega+\Delta\omega x2$. A frequency shifter 122y1 provided on the optical path of the first light beam Ly1 shifts the frequency of the first light beam Ly1 by a predetermined amount $\Delta\omega y1$ so that the center frequency of the first light beam Ly1 becomes $\omega+\Delta\omega y1$. A frequency shifter 122y2 provided on the optical path of the second light beam Ly2 shifts the frequency of the second light beam Ly2 by a predetermined amount $\Delta\omega y2$ so that the center frequency of the second light beam Ly2 becomes $\omega+\Delta\omega y2$.

The rod lens 153x is optically connected to the rod lens 151x by way of an optical fiber 156x. The frequency-shifted first light beam Lx1 at frequency $\omega+\Delta\omega x1$ passing through the half-silvered mirror 130 is condensed by the rod lens 153x and enters the optical fiber 156x. Then the first light beam Lx1 propagates through the optical fiber 156x, exits from the rod lens 151x and impinges upon an irradiating point on the object 120 through the condenser lens 134.

The rod lens 154x is optically connected to the rod lens 152x by way of an optical fiber 157x. The frequency-shifted second light beam Lx2 at frequency $\omega+\Delta\omega x2$ reflected by the half-silvered mirror 131a is condensed by the rod lens 154x and enters the optical fiber 157x. Then the second light beam Lx2 propagates through the optical fiber 157x, exits from the rod lens 152x and impinges upon the irradiating point on the object 120 through the condenser lens 134.

The rod lens 153y is optically connected to the rod lens 151y by way of an optical fiber 156y. The frequency-shifted first light beam Ly1 at frequency $\omega+\Delta\omega y1$ reflected by the half-silvered mirror 131b is condensed by the rod lens 153y and enters the optical fiber 156y. Then the first light beam Ly1 propagates through the optical fiber 156y, exits from the rod lens 151y and impinges upon the irradiating point on the object 120 through the condenser lens 134.

The rod lens 154y is optically connected to the rod lens 152y by way of an optical fiber 157y. The frequency-shifted second light beam Ly2 at frequency $\omega+\Delta\omega y2$ reflected by the half-silvered mirror 131c is condensed by the rod lens 154y and enters the optical fiber 157y. Then the second light beam Ly2 propagates through the optical fiber 157y, exits from the rod lens 152y and impinges upon the irradiating point on the object 120 through the condenser lens 134.

The rod lens 155 is connected to the condenser lens 137 by way of an optical fiber 158. The scattered first and second light beams Lx1, Ly1, Lx2 and Ly2 (the combined scattered light beam $L_S$) scattered by the object 120 and the half-silvered mirror 135 and condensed by the condenser lenses 136 and 137 propagates through the optical fiber 158 and exits from the rod lens 155 to impinge upon the photodetector 113.

In this embodiment, since the optical elements mounted on the pickup 170 and those outside the pickup 170 are connected through the flexible optical fibers, the first and second light beams can be caused to two-dimensionally scan the object 120 by moving the pickup 170.

Figure 14:
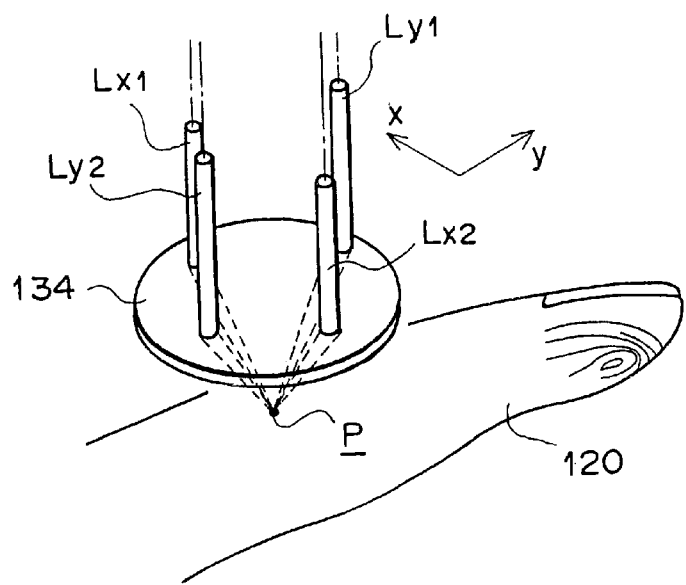
FIG. 14 is a view showing a part of the optical path of the measuring light beam in the blood vessel imaging system of the fifth embodiment.

The rod lenses 151x, 152x, 151y and 152y fixed to the pickup 170 are arranged so that light beams Lx1, Lx2, Ly1 and Ly2 exiting from the respective rod lenses travel as shown in FIG. 14. That is, the directions in which the first and second light beams Lx1 and Lx2 of the first optical system 111x impinge upon the irradiating point P are directions which extend along a x-direction on a plane opposed to the irradiating point P (e.g., a plane perpendicular to the optical axis of the condenser lens 134) when projected onto the plane, and the directions in which the first and second light beams Ly1 and Ly2 of the first optical system 111y impinge upon the irradiating point P are directions which extend along a y-direction perpendicular to the x-direction on the plane when projected onto the plane.

As in the third and fourth embodiments described above, the directions in which the first and second light beams Lx1 and Lx2 (Ly1 and Ly2) of each of the first optical systems 111x and 111y are opposite to each other and the first and second light beams travel along the optical axis of the condenser lens 134 after scattered at the irradiating point P.

Figure 15:
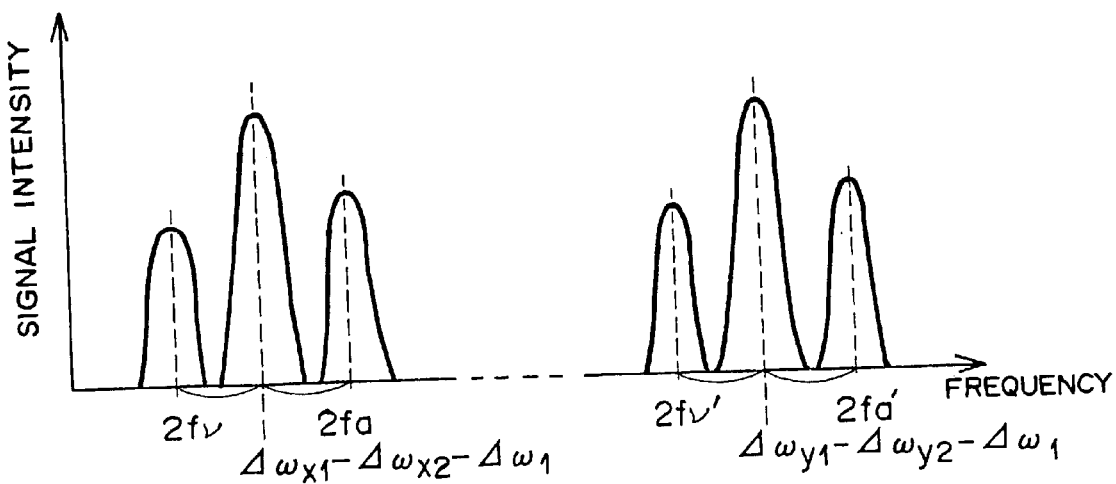
FIG. 15 is a schematic view for illustrating the waveform of the beat signal in the blood vessel imaging system of the fifth embodiment.
Figure 16:
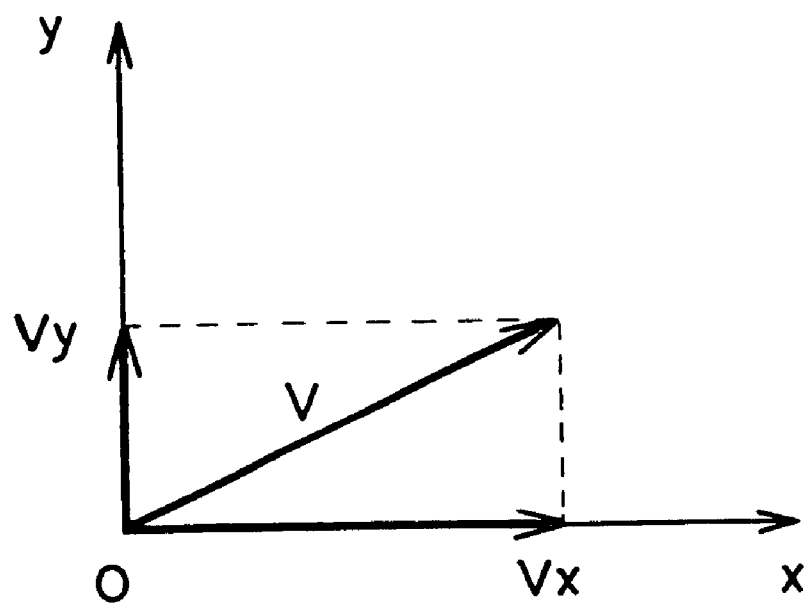
FIG. 16 is a schematic view for illustrating components of the flow rate of blood in directions perpendicular to each other.
Figure 17:
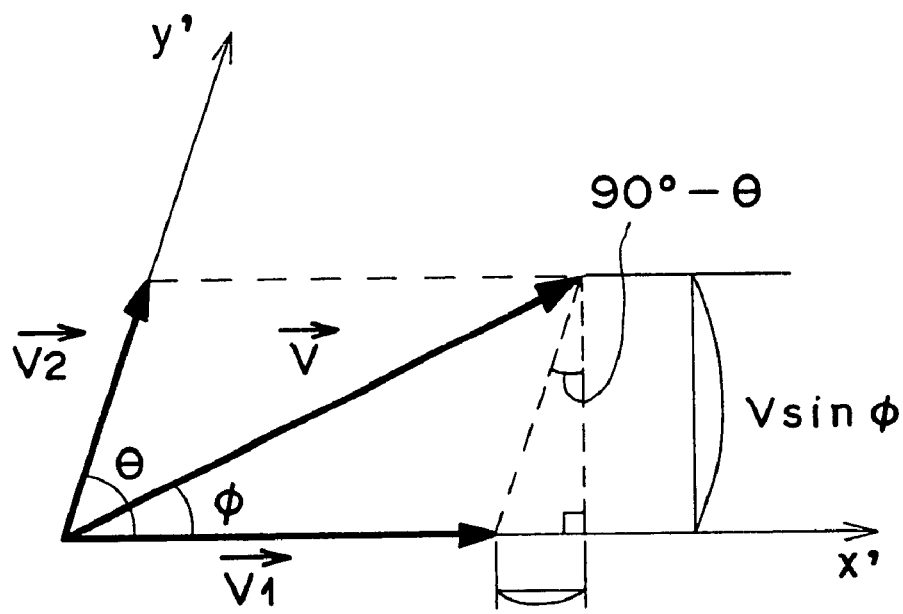
FIG. 17 is an explanatory view showing components of a flow rate of blood in two different directions.

In this embodiment, the waveform of the beat signal I obtained is as shown in FIG. 15. That is, when the measuring light beam is being projected onto an artery part, beat components at frequency ($\Delta\omega x1-\Delta\omega x2-\Delta\omega 1+2fa$) generated by the first optical system 111x together with beat components at frequency ($\Delta\omega y1-\Delta\omega y2-\Delta\omega 1+2fa'$) generated by the first optical system 111y. On the other hand, when the measuring light beam is being projected onto a vein part, beat components at frequency ($\Delta\omega x1-\Delta\omega x2-$ Δω1−2fv) generated by the first optical system 111x together with beat components at frequency (Δωy1−Δωy2−Δω1+2fv') generated by the first optical system 111y.

In this case, the personal computer 115 generates an image signal on the basis of the value of $fx^2+fy^2$ wherein fx and fy represent the frequency deviations of the beat components generated by the respective optical interference systems. That is, the personal computer 115 generates an image signal on the basis of the value of $fa^2+fa'^2$ when beat components at frequency (Δωx1−Δωx2−Δω1+2fa) and beat components at frequency (Δωy1−Δωy2−Δω1+2fa') are detected, and on the basis of the value of $fv^{2+fv'2}$ when beat components at frequency (Δωx1−Δωx2−Δω1−2fv) and beat components at frequency (Δωy1−Δωy2−Δω1−2fv') are detected.

With this arrangement, the same effect as when the directions in which the first and second light beams impinge upon the irradiating point are set parallel to the direction of flow of blood in the preceding embodiments can be obtained, and accordingly, the pickup 170 need not be able to rotate.

What is claimed is:

1. A blood vessel imaging system comprising:
   a measuring light source which emits a measuring light beam;
   an optical homodyne interference system which splits first and second light beams from the measuring light beam, causes the first and second light beams to impinge upon the same irradiating point on an organism in different directions, and combines together the first and second light beams scattered at the irradiating point into a combined scattered light beam having homodyne beat components
   a scanning means which causes the first and second light beams to scan the organism;
   an optical heterodyne detection system including an optical heterodyne interference system which splits a third light beam from the measuring light beam and combines the third light beam with the combined scattered light beam emanating from the optical homodyne interference system into a combined output light beam, a frequency shifter which causes a frequency difference between the third light beam and the first and second light beams, and a beat component detecting means which detects beat components of the combined output light beam and outputs a heterodyne beat component detection signal, and
   an image signal generating means which generates an image signal on the basis of the frequency of the homodyne beat components, generated by the optical homodyne interference system, included in the heterodyne beat component detection signal output from the optical heterodyne detection system.

2. A blood vessel imaging system as defined in claim 1 in which the image signal generating means generates an image signal representing an artery part of the organism when the frequency of the homodyne beat components generated by the optical homodyne interference system is higher than a predetermined threshold value.

3. A blood vessel imaging system as defined in claim 1 or 2 in which the image signal generating means generates an image signal representing a vein part of the organism when the frequency of the homodyne beat components generated by the optical homodyne interference system is not higher than a predetermined threshold value.

4. A blood vessel imaging system as defined in claim 1 or 2 further comprising a position adjustment means which adjusts the positions of the organism and the optical homodyne interference system relative to each other to change the directions of incidence to the irradiating point of the first and second light beams.

5. A blood vessel imaging system as defined in claim 1 or 2 in which
   the system further comprises an in-phase time detecting means for detecting in-phase times, at which the flow rate of blood in the blood vessel to be imaged becomes a predetermined value, and outputting a timing signal, and
   the image signal generating means samples the beat component detection signal at times, at which the flow rate of the blood is substantially maximized, on the basis of the timing signal and generates the image signal on the basis of the sampled beat component detection signal.

6. A blood vessel imaging system as defined in claim 5 in which the in-phase time detecting means is a means for detecting a pulse wave of the organism.

7. A blood vessel imaging system as defined in claim 5 in which the in-phase time detecting means is a means for detecting the times at which the frequency of the homodyne beat components generated by the optical heterodyne interference system takes a peak value.

8. The system of claim 1, wherein the first and second light beams comprise light beams of the same frequency characteristics and impinge upon said organism.

9. The system of claim 2, wherein a determination of an artery part is based on the frequency of the homodyne beat component, regardless of an amplitude of the homodyne beat component.

10. The system of claim 3, wherein a determination of a vein part is based on the frequency of the homodyne beat component, regardless of an amplitude of the homodyne beat component.

* * * * *